United States Patent [19]

Hasegawa et al.

[11] 4,450,234

[45] May 22, 1984

[54] ANTIBIOTIC C-15003 PHM AND PRODUCTION THEREOF

[75] Inventors: Toru Hasegawa, Kawanishi; Motowo Izawa, Amagasaki; Seiichi Tanida, Nagaokakyo, all of Japan

[73] Assignee: Takeda Chemical Industries, Ltd., Osaka, Japan

[21] Appl. No.: 347,724

[22] Filed: Feb. 10, 1982

Related U.S. Application Data

[62] Division of Ser. No. 188,242, Sep. 17, 1980, Pat. No. 4,331,598.

[30] Foreign Application Priority Data

Sep. 19, 1979 [JP] Japan .................................. 54-121234

[51] Int. Cl.$^3$ ........................... C12N 1/20; C12R 1/365
[52] U.S. Cl. ....................................... 435/253; 435/872
[58] Field of Search ........................ 435/119, 253, 872

[56] References Cited

U.S. PATENT DOCUMENTS

| | | | |
|---|---|---|---|
| 4,151,042 | 4/1979 | Higashide et al. | 435/872 |
| 4,162,940 | 7/1979 | Higashide et al. | 435/119 |
| 4,292,309 | 9/1981 | Higashide et al. | 435/253 |
| 4,320,200 | 3/1982 | Higashide et al. | 435/253 |
| 4,373,028 | 2/1983 | Higashide et al. | 435/253 |

*Primary Examiner*—Esther M. Kepplinger
*Attorney, Agent, or Firm*—Wegner & Bretschneider

[57] ABSTRACT

Novel antibiotic C-15003 PHM, which is produced by cultivating a microorganism belonging to the genus Nocardia and being capable of producing antibiotic C-15003 PHM, and novel C-15003 PHM acylate, which is produced by subjecting C-15003 PHM thus obtained to acylation reaction with an acylating agent, have antiprotozoan and antitumor activities.

1 Claim, No Drawings ium to have C-15003 PHM elaborated and accumulated in
ANTIBIOTIC C-15003 PHM AND PRODUCTION THEREOF This application is a divisional of application Ser. No. 188,242 filed Sept. 17, 1980, U.S. Pat. No. 4,331,598.

The present invention relates to C-15003 PHM, which is a novel substance, and a method of producing the same.

The present inventors obtained a variety of soil and other samples, screened the microorganisms isolated from the samples and their artificially induced mutants for substances which those microorganisms and mutants elaborated, and found that some of the microorganisms would produce a novel substance C-15003 PHM, that by cultivating such microorganisms in appropriate culture media, it was possible to cause said substance to be elaborated and accumulated in the resultant fermentation broths, that useful derivative compounds could be produced from said substance, and that another group of the microorganisms was capable of producing C-15003, maytansinol propionate, maytanacine and maytansinol which are known compounds. The above findings were followed by further research which has resulted in this invention.

This invention is therefore directed to
(1) a method of producing C-15003 PHM, characterized by cultivating a C-15003 PHM-producing strain of the genus Nocardia in a culture medium to have C-15003 PHM elaborated and accumulated in the resultant fermentation broth and harvesting the same substance from said broth;
(2) a method of producing C-15003, maytansinol propionate, maytanacine and maytansinol, characterized by cultivating Nocardia sp. No. N-1231 in a culture medium to have C-15003, maytansinol propionate, maytanacine and maytansinol elaborated and accumulated in the resultant fermentation broth and harvesting the same substances from said broth;
(3) Nocardia sp. No. N-1231, which is deficient in the ability to produce C-14482 and capable of producing C-15003 PHM; and
(4) C-15003 PHM and its acylate, which are represented by the formula:

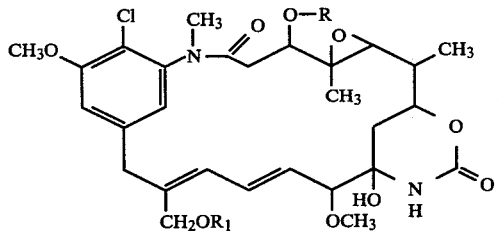

wherein R is —COCH$_3$, —COCH$_2$CH$_3$,

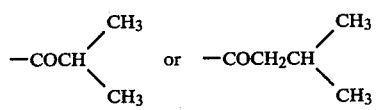

and R$_1$ is hydrogen or R$_2$CO— in which R$_2$ is phenyl or alkyl of 1 to 5 carbon atoms, the alkyl being optionally substituted by phenyl.

The term 'C-15003 PHM' as used throughout this specification means either all the compounds of formula (I) wherein R$_1$ is hydrogen generally or any one of the same compounds severally and independently. It should also be understood that in formula (I), the compound wherein R is —COCH$_3$ and R$_1$ is hydrogen will be referred to as C-15003 PHM-1 or merely as PHM-1, the compound wherein R is —COCH$_2$CH$_3$ and R$_1$ is hydrogen as C-15003 PHM-2 or merely as PHM-2, the compound wherein R is

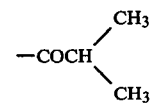

wherein R$_1$ is hydrogen as C-15003 PHM-3 or merely as PHM-3, and the compound wherein R is

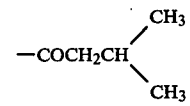

and R$_1$ is hydrogen as C-15003 PHM-4 or merely as PHM-4.

It should also be understood that the term 'C-15003' is used herein to denote all the compounds of the following formula (II) generally or any one of the same compounds severally and independently.

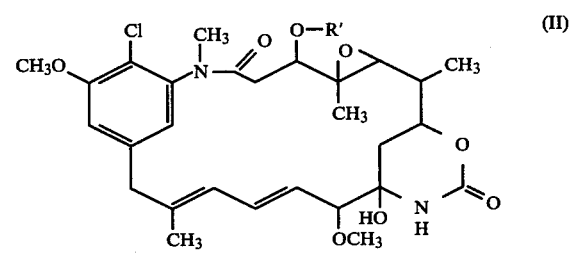

wherein R' is

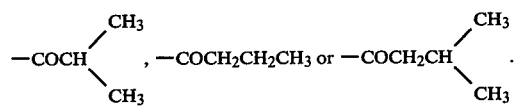

Referring to the above formula (II), the compound wherein R' is

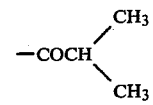

will hereinafter be referred to as C-15003 P-3 or merely as P-3, the compound wherein R' is —COCH$_2$CH$_2$CH$_3$ as C-15003 P-3' or merely as P-3', and the compound wherein R' is

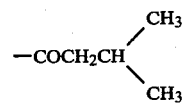

as C-15003 P-4 or merely as P-4.

It is further understood that in this specification, maytansinol will sometimes be referred to briefly as P-0, maytanacine as P-1 and maytansinol propionate as P-2.

The above-mentioned P-0, P-1 and P-2 are the compounds described in Journal of the American Chemical Society 97, 5294 (1975) and U.S. Pat. No. 4,151,042, and P-3, P-3' and P-4 are the compounds described in Nature, vol. 270, P. 721 (1977), Tetrahedron 35, 1079 and U.S. Pat. No. 4,162,940.

It should also be understood that the term 'C-14482' is used herein to mean all of $C-14482A_1$, $B_1$, $B_2$ and $B_3$ generally or any of these compounds severally and independently. $C-14482A_1$ is the compound described in Patent Application in the Federal Republic of Germany Laid-Open as Offenlegungsschrift No. 2833689.

$C-14482B_1$, $B_2$ and $B_3$ have been described in Patent Application in the Federal Republic of Germany Laid-Open as Offenlegungsschrift No. 3003359. Further, C-14482B means all of $C-14482B_1$, $B_2$ and $B_3$ generally or any one of the same compounds severally and independently.

The microorganism which can be utilized for the production of C-15003 PHM (hereinafter referred to sometimes as C-15003 PHM-producing strain) may be any organism that belongs to the genus Nocardia and is capable of producing C-15003 PHM. As an example of such organism may be mentioned Nocardia sp. No. N-1231 (hereinafter referred to sometimes as No. N-1231 strain) which is an artificial mutant derived by the ordinary mutagenic technique from the parent strain Nocardia sp. No. C-14482 IFO-13725 which is an Actinomycete separated by us in the course of screening of microorganisms for antibiotic producers. The particular microorganism mentioned above has the following characteristics.

The present inventors investigated the microbiological characteristics of No. N-1231 strain in accordance with the procedure of Schirling & Gottlieb [International Journal of Systematic Bacteriology 16, 313–340 (1966)]. The results of observation at 28° C. over 21 days are as follows.

(1) Morphological Characteristics

The vegetative mycelium is colorless to light yellow or orange yellow, and extends well and branches out both on agar and in liquid media. Many of the vegetative hyphae are 0.5 to 1.2 μm in diameter and, in later stages of culture, become fragmented into rods, elongated rods or branched hyphae. This strain gives good growth on various taxonomic media. The aerial mycelium develops as superimposed on the vegetative mycelium but a number of coremia-like bodies (50–180 μm × 400–1500 μm) are formed so that frequently it appears to have grown on such coremia-like bodies. Many of the aerial hyphae are bent or linear and a loosely spiral configuration is observed in rare cases. Microscopic observation of an old culture of this strain shows few chains of spores. Thus, the formation of conidia or spores is sparse. Microscopic observation of spores taken from a surface of the culture reveals a large number of oblong (0.5–1.2 μm × 4.8–6.8 μm) and ellipsoidal (0.8–1.2 μm × 1.5–4 μm) bodies resembling divided cells or arthrospores and an electronmicrograph of these bodies shows that their surfaces are flat and smooth. The development of aerial mycelium is generally poor and on many of the media used, fair aerial growth is noted up to 3 to 7 days of cultivation but tends to disappear as the culture becomes aged, i.e. after 10 days of cultivation.

When the strain is cultivated in a liquid medium, there is a phase in which it displays motility, and during that time, polymorphism is seen such that the hyphae are rod-shaped, branched rods and elongated rods occurring singly, in chains or further branched. As electronmicrograph of those hyphae shows a number of elongated flagella around the cells.

(2) Constituents of cells

The strain was shake-cultured in ISP No. 1 Modified Medium at 28° C. for 66 to 90 hours and when the organisms had grown sufficiently and reached a stationary phase, the mycelia were collected and rinsed. The above mycelia were assayed for cellular diaminopimelic acid and sugar by the method of B. Backer et al (Applied Microbiology 12, 421, 1964) and the method of M. B. Lechevalier (*Journal of Laboratory and Clinical Medicine* 71, 934, 1968). The results indicated that the former is the meso-compound and, as to the latter, spots were detected which corresponded to galactose and arabinose. Further, in accordance with the method of B. Beckers et al (Applied Microbiology 17, 236, 1965), cell wall specimens were prepared and tested for diaminopimelic acid, sugar and amino acids. It was found that the detected diaminopimelic acid was the meso-compound and, as for sugar, the presence of a large amount of galactose was noted but there was no evidence of arabinose. As regards amino acids, glutamic acid and alanine were clearly in evidence but lysine and glycine were detected only in trace amounts.

(3) Cultural characteristics on taxonomic media

On various media, this strain invariably gives good growth and its vegetative mycelium is colorless to light yellow in young cultures but assumes a light yellow-brown to yellow-brown color in aged cultures. In the great majority of taxonomic media, the strain does not produce soluble pigments, but light brown soluble pigmentation is observed in a few media. The aerial mycelium is powdery and generally shows moderate growth, its color being white to yellow or light yellowish brown. The aerial mycelium disappears on prolonged culture in many media (approx. 2 weeks or longer) and, instead, the vegetative mycelium begins to have a glossy surface. The cultural characteristics of this strain on taxonomic media are presented in Table 1.

TABLE 1

Culture characteristics of No. N-1231 on taxonomic media

| | |
|---|---|
| (a) | Sucrose nitrate agar<br>Growth (G): sparse, thin, colorless<br>Aerial mycelium (AM): scanty, white<br>Soluble pigment (SP): none |
| (b) | Glucose nitrate agar<br>G: sparse, thin, colorless<br>AM: scanty, white<br>SP: none |
| (c) | Glycerol nitrate agar<br>G: moderate, colorless to light yellow (3 ea or 2 ga)* or bright yeilow (3 ia)*, coremia-like bodies formed<br>AM: scanty, white to light yellow (3 ea)*<br>SP: none |
| (d) | Glucose asparagine agar<br>G: moderate, colorless to yellow (3 ga)*<br>AM: scanty, light yellow (3 ea)*<br>SP: none |
| (e) | Glycerol asparagine agar<br>G: moderate, colorless to yellow (3 ga)*<br>AM: moderate, white to light yellowish brown (2 ea)* |

TABLE 1-continued

Culture characteristics of No. N-1231 on taxonomic media

SP: none
(f) Nutrient agar
  G: moderate, colorless to light yellowish brown (2 ca)* or yellow (3 ga)*
  AM: none
  SP: none
(g) Calcium malate agar
  G: moderate, colorless to yellow (3 ga)* or bright yellow (3 pa)*, coremia-like bodies formed
  AM: scanty, white
  SP: none
(h) Yeast extract-malt extract agar
  G: luxuriant, colorless to yellow (3 ga)* or bright yellowish brown (3 la)*, coremia-like bodies formed
  AM: moderate, white to cream (3 ca)* or light yellow (3 ea)*
  SP: pale yellowish brown
(i) Oatmeal agar
  G: moderate, colorless to yellow (3 ga)* or light yellowish brown (2 ca)*
  AM: moderate, white to light yellow (3 ea)* or cream (3 ca)*
  SP: none, or pale yellowish brown
(j) Starch agar
  G: moderate, colorless to yellow (3 ga or 2 ga)*
  AM: poor, white to light yellow (3 ea)*
  SP: none
(k) Peptone-yeast extract iron agar
  G: moderate, coloress to yellow (3 ig)* or bright yellowish brown (3 la)*
  AM: none or poor, white
  SP: pale yellowish brown
(l) Tyrosine agar
  G: moderate, colorless to yellow (3 ig)* or bright yellowish brown (3 la)*, coremia-like bodies formed
  AM: poor, cream (3 ca)* or bright yellowish brown (3 la)*
  SP: light yellowish brown (purplish)

*The color codes according to Color Harmony Manual, 4th Ed. (published from Container Corporation of America, 1958)

(4) Physiological Characteristics

The physiological characteristics of this strain are shown in Table 2. Thus, the strain gives growth in the temperature range of 12° to 38° C., and produces aerial mycelium well on agar medium (ISP No. 2) and 20° to 35° C.

TABLE 2

| Physiological characteristics of No. N-1231 | |
|---|---|
| Temperature range for growth: | 12° C.–38° C. |
| Temperature range for production of aerial mycelium: | 20° C.–35° C. |
| Liquefaction of gelatin: | very weak |
| Hydrolysis of starch: | positive |
| Reduction of nitrates: | positive |
| Peptonization of milk: | positive |
| Coagulation of milk: | negative |
| Decomposition of casein: | positive |
| Production of melanoid pigment: | |
| (peptone-yeast extract iron agar): | negative |
| (tyrosine agar): | negative |
| Decomposition of tyrosine: | positive |
| Decomposition of xanthine: | negative |
| Decomposition of hypoxanthine: | negative |
| Resistance to lysozyme: | positive |
| Resistance to sodium chloride: | 2% |

(5) Utilization of Carbon Sources

The carbohydrate assimilation of this strain was determined by the method of Pridham and Gottlieb (Journal of Bacteriology 56, 107, 1948) using the medium described therein and the basal medium supplemented with 0.1% of yeast extract (Difco, U.S.A.). The results are shown in Table 3.

TABLE 3

| Utilization of carbon sources by No. N-1231 | | |
|---|---|---|
| Carbon Source | Growth | |
| D-xylose | + | ++* |
| L-arabinose | − | + |
| D-glucose | ++ | ++ |
| D-galactose | ++ | ++ |
| D-fructose | +++ | +++ |
| L-rhamnose | ++ | + |
| D-mannose | ++ | +++ |
| Sucrose | ++ | ++ |
| Lactose | ± | − |
| Maltose | + | ++ |
| Trehalose | ++ | ++ |
| Raffinose | ± | − |
| Mellibiose | ± | ± |
| i-Inositol | − | ± |
| D-sorbitol | − | ± |
| D-mannitol | ++ | ++ |
| Glycerol | ++ | +++ |
| Soluble starch | + | ++ |
| Control | − | − |

*Basal medium plus 0.1% yeast extract
Notes:
+++: Good growth
++: Fair growth
+: Growth noted
±: Slight growth
−: No growth

(6) Other characteristics

Gram-staining of the vegetative mycelium of this strain gives positive.

The above-described characteristics of this strain were compared with the corresponding descriptions in S. A. Waksman: The Actinomycetes Vol. 2, The Williams and Wilkins Company, 1961, R. E. Buchanan and N. E. Gibbons (ed.): Bergey's Manual of Determinative Bacteriology 8th ed., 1974, and other literature.

As mentioned hereinbefore, this strain (1) is fragmented at later stages of culture into rods or elongated rods, with branched versions of such rods being observed, (2) gives little evidence of discrete conidia or spores, and tends to yield colonies having a skinny or cursted surface on agar, with a gloss comparable to that of general bacteria. These features suggest that the strain can be roughly relegated to Group III of the genus Nocradia. However, because its cultural characteristics on taxonomic media, physiological characteristics, motile cells and cell wall composition differentiate from any known strain, it was determined to be a novel species of the genus Nocardia.

The present No. N-1231 strain has been deposited Institute for Fermentation, Osaka, Japan, on Aug. 20, 1979, under the accession number of IFO 13963; the Fermentation Research Institute, Agency of Industrial Science and Technology, Tukuba, Japan, on Aug. 29, 1979, under the accession number of FERM-P No. 5185 and the American Type Culture Collection, U.S.A., on Sept. 11, 1979, under the number of ATCC 31565.

The No. N-1231 strain was obtained from the parent strain Nocardia sp. C-14482 IFO-13725 by the following procedure.

Monospores were taken from the parent strain, and a line having a high C-15003-producing ability was selected by using inhibitory activity against *Hamigera avellanea* IFO-7721 as an indicator. This line was cultivated in a liquid medium containing 5 μg/ml of ethidium bromide and the culture broth was filtered through Toyo Filter Paper No. 2. The filtrate was diluted and applied to a yeast extract-malt extract agar plate. The inoculated palte was incubated at 32° C. The multiplicity of resultant colonies are cultivated in a production medium and the mutant strains deficient in the ability to produce C-14482 were selected using inhibitory activity against *Proteus mirabilis* IFO-3849 as an indicator. From among these mutant strains, the No. N-1231 strain was isolated as the strain having the highest C-15003-producing ability.

While the characteristics of this strain No. N-1231 bear close resemblance with those of the parent strain Nocardia sp. No. C-14482 (c.f. German Patent Application Laid-open No. 2833689), there is a marked distinction therebetween in antibiotic production and production ability. Therefore, the present inventors identified the strain to be a new strain of the same species as Nocardia sp. C-14482 and named it Nocardia sp. No. N-1231.

The No. N-1231 strain, unlike its parent, is deficient in C-14482 production ability, and has the ability to produce C-15003. However, it is resistant to lincomycin, penicillin G and streptomycin, and in these and other taxonomical characteristics, the strain is similar to the parent strain.

Furthermore, the No. N-1231 strain is able to produce C-15003, P-2, P-1 and P-0 in high titers. It is also understood that Nocardia sp. No. C-14482 has the following and other distinct features.

(1) Gram-positive
(2) The vegetative mycelium extends well and is 0.5 to 1.2 $\mu$m in diameter.
It is partially fragmented into rods and elongated rods and shows motility. (However, some mutants are fragmented less extensively and others more extensively).
(3) The production of aerial mycelium varies with strains. Thus, while the strain normally produces white to yellow aerial mycelium, mutants give only scanty aerial mycelium.
(4) Motile hyphae are observed when the aerial mycelium has been suspended in liquid medium and allowed to stand at an appropriate temperature for about 30 minutes.
(5) The cell wall contains meso-diaminopimelic acid and galactose.

Microorganisms of the genus Nocardia, like other microorgansims in general, are subject to mutation, whether spontaneous or artificial. For example, a large number of mutants can be obtained from the parent strain by isolation of monospores irradiated with X-rays, gamma rays, ultraviolet light or other radiation, cultivation on media containing various mutagenic agents, and other means. These artificial mutants, as well as spontaneous mutants, can all be employed for the production of C-15003 PHM if they are not substantially distinct in comparison with the microbiological characteristics mentioned hereinbefore and those to be mentioned hereinafter and if they are able to produce C-15003 PHM. Thus, for example, by subjecting the No. N-1231 strain to various mutagenic treatments, there can be obtained a variety of mutants such as one giving a light yellow to light yellowish brown soluble pigment, one having a colorless vegetative mycelium, one having a reddish brown to orange red vegetative mycelium, one giving a yellowish green vegetative mycelium or soluble pigment, one producing an abundant white aerial mycelium and one whose hyphae are liable to be fragmented.

The medium employed for the cultivation of the C-15003 PHM-producing strain or No. N-1231 strain may be either a liquid medium or a solid medium, which contains nutrient sources which are available to the particular organisms, although a liquid medium is preferred for large-scale fermentation. Incorporated in the medium are the sources of carbon which the C-15003 PHM-producing strain or No. N-1231 strain is able to assimilate, the sources of nitrogen which are digestable to the strain, various inorganic substances and trace nutrients, all in suitable proportions. The sources of carbon include, among others, glucose, lactose, sucrose, maltose, dextrin, starch, glycerol, mannitol, sorbitol, oils and fats (e.g., soybean oil, lard oil, chicken oil, etc.), n-paraffin, etc. The sources of nitrogen include, among others, meat extract, yeast extract, dried yeast, soybean flour, corn steep liquor, peptone, cotton-seed flour, spent molasses, urea, ammonium salts (e.g. ammonium sulfate, ammonium chloride, ammonium nitrate, ammonium acetate, etc.) and others. Furthermore, salts of sodium, potassium, calcium, magnesium, etc., metal salts such as salts of iron, manganese, zinc, cobalt, nickel etc., salts of phosphoric acid, boric acid, etc., and salts of organic acids such as acetic acid, propionic acid, etc. can be employed. The medium may further contain amino acids (e.g. glutamic acid, aspartic acid, alanine, lysine, methionine, proline, etc.), peptides (e.g. dipeptides, tripeptides, etc.), vitamins (e.g. $B_1$, $B_2$, nicotinic acid, $B_{12}$, C, etc.), nucleic acids (e.g., purine, pyrimidine and their derivatives), etc. It is of course possible for the purpose of adjusting the pH of the medium, to add inorganic or organic acids and alkalis, buffers, etc. or, for defoaming purposes, to add suitable amounts of oils, fats, surface active agents, etc.

The cultivation of the microorganism may be performed by whatever method of cultivation, e.g. stationary culture, shake culture or aerobic stirring culture. For a high production run, submerged aerobic culture is preferred. While conditions of cultivation vary with the condition and composition of medium, the strain of microorganism, the cultivation procedure, etc., it is generally preferable to conduct the cultivation at 20° to 32° C. and an initial pH of near-neutrality. It is especially desirable to carry out the cultivation at 25° to 28° C. and an initial pH of 6.5 to 7.5. The cultivation time also varies with the above-mentioned conditions but the cultivation should be continued until the titer of the desired antibiotic has reached a maximum. The time till such a maximum titer is usually about 72 to 192 hours when shake culture or aerobic stirring culture is carried out in a liquid medium.

The culture broth obtained by the cultivation of the C-15003 PHM-producing strain in the above manner contains the novel substance C-15003 PHM which exists both in the liquid phase of the broth as well as in the mycelia.

To isolate the C-15003 PHM produced in the broth, the routine separation and purification procedures for neutral lipophilic microbial metabolites can be utilized, for the present substance is also neutral fat-soluble. Thus, for example, a procedure utilizing its different solubility from that of impurity, a procedure utilizing a different adsorptive affinity for various adsorbents such as activated carbon, macroporous nonionic resin, silica gel, alumina, etc., and a procedure utilizing an ion exchange resin for removal of impurity may be utilized, either singly, in combination or in repetition. Since, as aforesaid, C-15003 PHM occurs both in the liquid phase of the broth and in the mycelium, the antibiotic is separated and purified by adsorption on an adsorbent either directly or after solvent extraction in the case of the liquid phase or after solvent extraction in the case of the mycelium. When a solvent extraction is performed, it is optional to (1) extract the total broth containing the mycelium or (2) extract each of the mycelium and filtrate after filtration or centrifugation. To extract the filtrate and mycelium independently, the following procedures can be followed with advantage.

The solvents suitable for extraction of the filtrate or the whole broth are water-immiscible organic solvents such as fatty acid esters (e.g. ethyl acetate, amyl acetate), alcohols (e.g. butanol), halogenated hydrocarbons (e.g. chloroform), and ketones (e.g. methyl isobutyl ketone). The extraction is performed in the neighborhood of neutrality and a preferred procedure comprises extracting a filtrate at pH 7 with ethyl acetate. The extract is washed with water and concentrated under reduced pressure and after the addition of a nonpolar solvent such as petroleum ether or n-hexane, a crude product (i) containing the activity is harvested. Since the TLC of this crude product shows a number of spots other than the spot assignable to C-15003 PHM, it is subjected to the following stepwise purification procedure. Thus, for routine use, various kinds of adsorption chromatography can be employed with advantage. The adsorbents for this purpose may be of the common varieties, such as silica gel, alumina, macroporous nonionic adsorbent resins, etc. Of these adsorbents, silica gel is the most effective for the purification of the crude product (i). The chromatogram may then be developed first with a nonpolar solvent such as petroleum ether or n-hexane and elution of C-15003 PHM be performed with the addition of a polar solvent such as ethyl acetate, acetone, ethanol, methanol, etc. As an example, silica gel (Merck, Germany, 0.05-0.2 mm) is used as the support and the desired column chromatography is performed with incremental mixtures of ethyl acetate and n-hexane. The eluate is assayed by TLC and the fractions containing C-15003 PHM are pooled and concentrated under reduced pressure, followed by addition of petroleum ether or n-hexane to obtain a crude product (ii). Because this product (ii) still contains impurities, further purification is carried out. Thus, for example, a second silica gel column is used with a different solvent system. The developing solvents for this purpose may be as follows. The column is first developed with a halogenated hydrocarbon such as dichloromethane or chloroform and, then, C-15003 PHM is separated with the addition of a polar solvent such as an alcohol (e.g. ethanol, methanol), a ketone (e.g. acetone, methyl ethyl ketone). The order of solvent systems for the first and second silica gel columns may be reversed and the organic solvents mentioned above may be replaced or used along with other organic solvents which are commonly used.

The C-15003 PHM fractions thus obtained are pooled, concentrated under reduced pressure, and after addition of 5 to 8 volumes, of ethyl acetate, allowed to stand, whereupon crystals of C-15003 PHM separate out. The crystals are further partitioned by means of the above-mentioned adsorbent. Thus, silica gel or macroporous nonionic adsorption resin can be used together with the solvent systems mentioned hereinbefore so as to obtain the desired eluate. When silica gel, for instance, is employed, a system of n-hexane and ethyl acetate or a system of chloroform and methanol is used as the eluent. In this case, compounds emerge from the column in the order of the compound of formula (I) having a largest number of carbon atoms in R. Therefore, each compound is detected by TLC and the corresponding fractions are pooled, concentrated under reduced pressure and treated with methanol or ethyl acetate to obtain a crop of crystals. The compounds can also be separated by preparative thin-layer chromatography on silica gel, in which case the portion of silica gel containing each fraction is scraped off and, after addition of a small amount of water, is extracted with ethyl acetate, concentrated under reduced pressure and treated with methanol or ethyl acetate to obtain crystals. The C-15003 PHM obtained in Example 5, which appears hereinafter, was dried under reduced pressure over phosphorus pentoxide at 60° C. for 8 hours. The physicochemical properties of the dried substance are shown hereinafter.

In order to isolate C-15003, P-2, P-1 and P-0 from a fermentation broth of No. N-1231 strain, the separation and purification procedures generally employed for the recovery of microbial metabolites can be utilized taking advantage of the fact that C-15003, P-2, P-1 and P-0 are neutral lipophilic. Thus, there can be employed, either alone or in combination or repetition, the procedure which takes advantage of a difference in solubility with respect to impurity, the procedure which utilizes differences in adsorptive affinity for adsorbent materials such as activated carbon, macroporous nonionic resin, silica gel, alumina, etc., the procedure for removing impurities by means of an ion exchange resin, and so forth. Since, as aforesaid, C-15003, P-2, P-1 and P-0 occur both in the liquid phase of the broth and in the mycelial portion, the filtrate is adsorbed directly or after solvent extraction on the adsorbent material, or the mycelium is adsorbed after solvent extraction on the adsorbent. The solvent extraction may be carried out in two alternative ways: (1) to extract the total fermentation broth including the mycelium with a solvent or (2) to separately extract the mycelium separated by filtration or centrifugation of the broth and the filtrate with a solvent. To extract the filtrate and mycelium separately, the following procedures can be carried out with advantage.

The solvent suitable for extraction from the filtrate includes water-immiscible organic solvents such as fatty acid esters (e.g. ethyl acetate, amyl acetate), alcohols (e.g. butanol), halogenated hydrocarbons (e.g. chloroform), ketones (e.g. methyl isobutyl ketone), etc. The extraction is carried out at pH near neutral and, preferably, the filtrate is adjusted to pH 7 and extracted with ethyl acetate. The extract is washed with water and concentrated under reduced pressure, followed by addition of a nonpolar solvent such as petroleum ether or n-hexane. In this manner, a crude product (i) containing the activity is recovered. Since this crude product gives a number of TLC spots other than those assignable to C-15003, P-2, P-1 and P-0, the following stepwise purification procedure is applied. Thus, as a purification procedure for routine use, various types of adsorption chromatography are effective and the adsorbents for this purpose may be the support materials generally employed, such as silica gel, alumina, macroporous nonionic adsorbent resin, etc. For purification from the crude product (i), silica gel is most effective and the column is developed first with a nonpolar solvent such as petroleum ether or n-hexane and, then, elution is carried out with the addition of polar solvents, for example ethyl acetate, acetone, ethanol and methanol in the mentioned order to obtain C-15003, P-2, P-1 and P-0 fractions, respectively. As an example, column chromatography is carried out with silica gel (Merck, Germany, 0.05-0.2 mm) as the support and with an increasing ethyl acetate to n-hexane ratio. The eluate is assayed by TLC and the fractions containing C-15003, P-2, P-1 and P-0 are pooled, concentrated under reduced pressure and treated with petroleum ether or n-hexane to obtain a crude product (ii). Since this product still contains impurities, the following purification procedure is carried out. Thus, for example, a further purification procedure comprises the use of a second silica gel column and a different solvent system. Thus, the column is first developed with a halogen-containing hydrocarbon such as dichloromethane, chloroform or the like and, then, elution is carried out with the addition of a polar solvent such as an alcohol (e.g. ethanol, methanol) or ketone (e.g. acetone, methyl ethyl ketone), whereby C-15003, P-2, P-1 and P-0 are respectively recovered. The order of solvent systems for the first and second columns may be reversed, and other organic solvents routinely used can be also utilized in suitable combinations.

When macroporous adsorbent resin is employed for the purification of crude product (ii), C-15003, P-2, P-1 and P-0 are eluted with a lower alcohol or a mixture of a lower ketone or ester with water. As examples of the lower alcohol, there may be mentioned methanol, ethanol, propanol, butanol, etc. The lower ketone may for example be acetone, methyl ethyl ketone or the like. The ester may for example be ethyl acetate. For example, the crude product (ii) is dissolved in 60% aqueous methanol and adsorbed on a column of Diaion HP-10 (Mitsubishi Chemical Industries Ltd., Japan). After the column is washed with 70% aqueous methanol, elution is carried out with 90% aqueous methanol. The procedure yields the desired compounds C-15003, P-2, P-1 and P-0.

What method has been employed, the resulting C-15003, P-2, P-1 and P-0 fractions are concentrated under reduced pressure, 5 to 8 volumes of ethyl acetate is added to each volume of the concentrate and the mixture is allowed to stand, whereupon crystals of C-15003, P-2, P-1 and P-0 separate out. The above crystals contain P-0, P-1, P-2, P-3, P-3' and P-4, which can be separated from each other by means of the above-mentioned adsorbents. Thus, silica gel or macroporous nonionic adsorbent resin can be used and fractional elution carried out with the solvents also mentioned hereinbefore. When silica gel is employed, by way of example, elution with n-hexane-ethyl acetate or chloroform-methanol gives P-4, P-3', P-3, P-2, P-1 and P-0 in that order. Therefore, after detection by TLC, P-4, P-3', P-3, P-2, P-1 and P-0 fractions are each concentrated under reduced pressure to obtain the corresponding crystals. When macroporous nonionic adsorbent resin is employed, gradient elution with alcohol, ketone or ester and water in a varying ratio or gradient elution with 60% aqueous methanol containing 5% of sodium chloride and 95% aqueous methanol, for instance, yields P-0, P-1, P-2, P-3, P-3' and P-4 in that order. Therefore, each of the fractions, after assaying by TLC, is concentrated under reduced pressure and crystallized from ethyl acetate.

The C-15003 PHM obtained according to Example 5, which appears hereinafter, has the following physical and chemical properties.

(a) PHM-4
$C_{33}H_{45}ClN_2O_{10} = 665.193$
m.p.: 190°-192° C.
Specific rotation: $[\alpha]_D^{24} -149° \pm 10°$ (C=0.23, ethanol),
Ultraviolet absorption spectrum: (methanol),
    232 nm ($\epsilon$ 25400),
    249 nm ($\epsilon$ 23600),
    280 nm ($\epsilon$ 4160),
    288 nm ($\epsilon$ 4220).
Infrared absorption spectrum: (KBr) (cm$^{-1}$)
    1740, 1646, 1582, 1152, 1112, 1091, 1040,
Mass spectrum: (m/e)
    664, 603, 568, 501, 486, 466.
Thin-layer chromatography: (Merck, silica gel glass plate, 0.25 mm)
    (a) Developing solvent: chloroform-methanol (9:1), Rf=0.31
    (b) Developing solvent: ($H_2O$-saturated ethyl acetate), Rf=0.19

(b) PHM-3
$C_{32}H_{43}ClN_2O_{10} = 651.167$
m.p.: 194°-192° C.
Specific rotation: $[\alpha]_D^{24} -148° \pm 10°$ (C=0.5, ethanol)
Ultraviolet absorption spectrum: (methanol)
    232 nm ($\epsilon$ 25600),
    249 nm ($\epsilon$ 23700),
    280 nm ($\epsilon$ 4190),
    288 nm ($\epsilon$ 4250).
Infrared absorption spectrum: (KBr) (cm$^{-1}$)
    1740, 1644, 1583, 1152, 1112, 1092, 1040.
Mass spectrum: (m/e)
    650, 589, 554, 501, 486, 466.
Thin-layer chromatography:
    (a) developing solvent: chloroform-methanol (9:1), Rf=0.30
    (b) developing solvent: ($H_2O$-saturated ethyl acetate), Rf=0.16.

(c) PHM-2
$C_{31}H_{41}ClN_2O_{10} = 637.141$
Mass spectrum: (m/e)
    636, 575, 540, 501, 486, 466
Thin-layer chromatography:
    (a) developing solvnet: chloroform-methanol (9:1), Rf=0.29
    (b) developing solvent: ($H_2O$-saturated ethyl acetate), Rf=0.13

(d) PHM-1
$C_{30}H_{39}ClN_2O_{10} = 623.115$
Mass spectrum: (m/e)
    622, 561, 526, 501, 486, 466
Thin-layer chromatography:
    (a) developing solvent: chloroform-methanol (9:1), Rf=0.27
    (b) developing solvent: ($H_2O$-saturated ethyl acetate), Rf=0.09

The above physicochemical properties of C-15003 PHM suggest easily that it is structurally similar to C-15003. The fact that the mass spectra of C-15003 PHM-4, PHM-3, PHM-2 and PHM-1 give m/e 501, 486 and 466 as common mass numbers indicates that these compounds have the same skeletal structure and are variant only in the kind of side chain ester residue. The fragment peaks M+-a (a=NHCO+H₂O), M+-(a+b) (b=R—OH) which are characteristic of maytansinoid compounds were found to be as follows.

|       | M⁺ − a | M⁺ − (a + b) | b   |
|-------|--------|--------------|-----|
| PHM-1 | 561    | 501          | 60  |
| PHM-2 | 575    | 501          | 74  |
| PHM-3 | 589    | 501          | 88  |
| PHM-4 | 603    | 501          | 102 |

Thus, the ester residues in 3-position were presumed to be acetyl for PHM-1, propionyl for PHM-2, isobutyryl for PHM-3 and isovaleryl for PHM-4. Further, comparison of C-15003 PHM-3 with the corresponding P-3 shows that whereas P-3 gives M+-a 573 and M+-(a+b) 485, PHM-3 gives 16 additional mass units for both, thus suggesting that PHM-3 is a compound including one oxygen atom as introduced into the skeletal moiety of P-3. Referring to the nuclear magnetic resonance spectra, P-3 gives methyl proton signals at δ 0.84, 1.21 and 1.71, while the signal at δ 1.71 is absent for PHM-3, it being therefore evident that the CH₃ group on C₁₄ has been converted to —CH₂—OH in PHM. The same can be said for PHM-4, PHM-2 and PHM-1. Therefore, the presumptive structures of PHM-4, PHM-3, PHM-2 and PHM-1 are as shown in FIG. 1.

FIG. 1

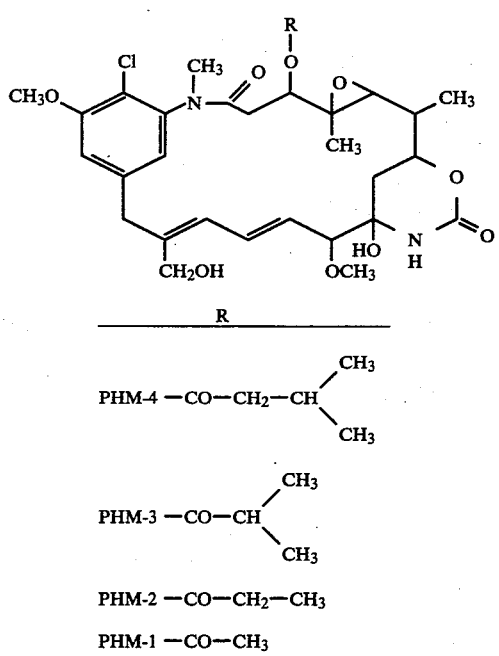

The species of C-15003 PHM are all new compounds and have antiprotozoan and antitumor activities. These compounds are useful also as starting materials for the production of beneficial derivatives.

Antimicrobial activity of C-15003 PHM:

Using Trypticase-soy-agar (Baltimore Biologicals, U.S.A.) as the assay medium, the growth inhibitory concentrations of the compound against the various microorganisms named hereinbelow were determined by the paperdisk method. Thus, on plate media containing the following microorganisms, respectively, minimal inhibitory concentrations were determined using paper disks imbibed with 0.02 ml of a 300 μg/ml solution of PHM-3 or PHM-4 (disks, Toyo Seisakusho, Japan, thin-type, diam. 8 mm). The results showed no activity against the following microorganisms.

*Escherichia coli, Proteus vulgaris, Proteus mirabilis, Pseudomonas aeruginosa, Staphylococcus aureus, Bacillus subtilis, Bacillus cereus, Klebsiella pneumoniae, Serratia marcessence, Mycobacterium avium.*

In addition, using *Tetrahymena pyriformis* W strain as the test organism and the assay medium composed of 20 g proteose peptone (Difco, U.S.A.), 1 g yeast extract, 2 g glucose, 1000 ml distilled water and 10 ml 1 M phosphate buffer, pH 7.0, cultivation was carried out at 28° C. for 44 to 48 hours and the growth inhibitory concentration of the antibiotic was determined by the serial broth dilution method. It was found that PHM-3 and PHM-4 inhibit growth of the same strain of microorganism at the concentrations of 40 μg/ml and 40 μg/ml, respectively.

It is therefore clear that C-15003 PHM can be used as an antiprotozoan agent. As an antiprotozoan agent, C-15003 PHM can be used advantagoeusly as a reagent for studying the bacterial ecology of a soil, activated sludge or animal body fluid sample, for instance. Thus, when it is desired to test the activity of bacteria to the exclusion of the activity of protozoa in the operation and analysis of an activated sludge system for waste water treatment, the compound permits selective growth of bacetrial flora in the sample without allowing the concomitant protozoas to grow. A specific procedure may comprise adding the test sample to a liquid or solid medium, then adding 0.1 ml of a 10% aqueous solution of methanol containing 500 to 2000 μg/ml of C-15003 PHM per ml of the medium and incubating the same medium.

The toxicity of C-15003 PHM is low.

Moreover, C-15003 PHM can be used also as an intermediate for the synthesis of useful drugs.

The compound (I) wherein R₁ is R₂CO— according to this invention can be obtained by acylating a compound (I) wherein R₁ is hydrogen, i.e. C-15003 PHM.

This acylation reaction can be accomplished for example by reacting C-15003 PHM with a carboxylic acid of the formula (III)

$$R_2CO—OH \qquad (III)$$

wherein R₂ has the same meaning as defined above, or a reactive derivative of carboxyl group thereof.

In the formulae (I) and (III), examples of the acyl group (R₂CO—) represented by R₁ may include acyl groups such as acetyl, propionyl, n-butyryl, isobutyryl, n-valeryl, isovaleryl, caproyl, benzoyl, phenylacetyl and α-phenylpropionyl.

An exemplary acylation procedure comprises acylating C-15003 PHM with said acylating agent (III) in the presence or absence of a carbodiimide.

The carboxylic acid (III) may be used in a proportion of about 1 to 500 molar equivalents, preferably about 1 to 30 molar equivalents, relative to the starting compound (C-15003 PHM).

Said carbodiimide may be used in a proportion of about 1 to 700 molar equivalents and, preferably, about 1 to 50 equivalents, relative to the starting compound. The carbodiimide that can be employed is any compound containing a carbodiimide bond (—N=C=N—) which is convertible to a urea bond in the course of reaction, and may for example be a compound of the following formula $$R_3—N=C=N—R_4 \qquad (IV)$$

[wherein $R_3$ and $R_4$ each means an organic residue conducive to a convertion of the carbodiimide bond into a urea bond in the present acylation reaction].

As examples of organic residues $R_3$ and $R_4$ there may be mentioned $C_{3-7}$ cycloalkyl groups which may optionally have di-lower ($C_{1-6}$; the same applies hereinafter) alkyl amino; lower alkyl groups which may optionally have di-lower alkylamino or morpholino, and phenyl groups which may optionally have lower alkyl. The carbodiimide preferred for commercial production is dicyclohexylcarbodiimide, although use may also be made of diphenylcarbodiimide, di-o-tolylcarbondiimide, di-p-tricarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide, 1-ethyl-3-(3-dimethylaminopropyl)carbodiimide, etc.

This acylation reaction may be carried out in an appropriate solvent, such as esters (e.g. ethyl acetate), ethers (e.g. diethyl ether, dioxane, tetrahydrofuran), halogenated hydrocarbons (e.g. methylene chloride, chloroform), nitriles (e.g. acetonitrile), aromatic hydrocarbons (e.g. benzene), nitromethane, pyridine, dimethylformamide, dimethyl sulfoxide, sulfolane, etc. inclusive of suitable mixtures of such solvents.

The acylation reaction may be carried out at a suitable temperature, usually from ice-cooling up to the reflux temperature of the reaction system.

The acylation reaction proceeds with further advantage in the presence of a catalyst assisting in acylation. Thus, for example, a basic catalyst or an acid catalyst may be utilized. The basic catalyst is exemplified by tertiary amines [such as aliphatic tertiary amines, e.g. triethylamine; and aromatic tertiary amines, e.g. pyridine, $\alpha$-, $\beta$- or $\gamma$-picoline, 2,6-lutidine, 4-dimethylaminopyridine, 4-(1-pyrrolidinyl)-pyridine, dimethylaniline, diethylaniline], alkali metal halides (e.g. potassium fluoride, lithium iodide anhydrate), organic acid salts (e.g. sodium acetate) and so on. The acid catalyst is exemplified by Lewis acids [e.g. zinc chloride anhydrate, aluminum chloride anhydrate ($AlCl_3$), tin tetrachloride ($SnCl_4$), antimony pentachloride, cobalt chloride, cupric chloride, boron trifluoride etherate], inorganic strong acids (e.g. sulfuric acid, perchloric acid, hydrogen chloride, hydrogen bromide), organic stron acids (e.g. benzenesulfonic acid, p-toluenesulfonic acid, trifluoroacetic acid, trichloroacetic acid), acidic ion exchange resin (e.g. polystyrenesulfonic acid), etc. Among the above catalysts, 4-dimethylaminopyridine, 4-(1-pyrrolidinyl)pyridine, etc. are preferred.

The catalyst may be used in a catalytic amount i.e. an amount sufficient to promote the acylation of C-15003 PHM with carboxylic acid (III), i.e. usually from about 0.001 to 10 molar equivalents and preferably from about 0.01 to 1 molar equivalent based on compound (III). In many instances, the use of such a catalyst causes a substantial increase in the yield of compound (I) wherein $R_1$ is $R_2CO$—. It also helps realize savings in the amount of carboxylic acid (III); for example, to reduce the amount of (III) to about 1 to 10 molar equivalents relative to starting compound (I).

The acylation reaction using a reactive derivative of carboxyl group of carboxylic acid (III) may for example be an acylation with a derivative having a functional group capable of acylating the —$CH_2OH$ in the 14-position of starting compound (I) wherein $R_1$ is hydrogen, such as an acid anhydride, acid halide (e.g. chloride, bromide), active amide or active ester of carboxylic acid (III). The solvent and catalyst for this acylation procedure may be those mentioned for acylation in the presence of a carbodiimide reagent. The reaction temperature may usually range from about $-40°$ C. to $+100°$ C., preferably about $-20°$ C. to $+40°$ C., although further heating may be applied in order to increase the reaction rate.

The compound (I) wherein $R_1$ is $R_2CO$— produced in the above manner can be isolated from the reaction mixture by the known procedure such as concentration, extraction with a solvent, chromatography, recrystallization, etc. The compounds obtainable upon acetylation of the 14—$CH_2OH$ of C-15003 PHM have marked antiprotozoan and antitumor activities.

Using Trypticase-soy-agar (Baltimore Biologicals, U.S.A.) as the test medium, the growth inhibitory activity of the compound against the organisms named below was assayed by the paper disk method. Thus, on the plate media each containing one of the undermentioned organisms, the activity of the compound was tested using paper disks (Toyo Seisakusho, Japan, thin type, diam. 8 mm) imbibed with 0.02 ml of a 300 $\mu g/ml$ solution of PHM-3-acetate. It was found that the above compound failed to show activity against the following organisms.

*Escherichia coli, Proteus vulgaris, Proteus mirabilis, Pseudomonas aeruginosa, Staphylococcus aureus, Bacillus subtilis, Bacillus cereus, Klebsiella pneumoniae, Serratia marcescence, Mycobacterium avium.*

*Tetrahymena pyriformis* W, as the test organism, was cultivated on an assay medium [20 g of proteose-peptone (Difco, U.S.A.), 1 g of yeast extract, 2 g of glucose, 1000 ml of distilled water, 10 ml of 1 M phosphate buffer, pH 7.0] at 28° C. for 44 to 48 hours and the growth inhibitory activity of the compound against the above-mentioned strain was assayed by the serial dilution method. It was found that PHM-3-acetate, which was obtained upon acetylation of 14—$CH_2OH$ of PHM-3, inhibits growth of the same organism at the concentration of 8 $\mu g/ml$.

It is thus evident that the present PHM acyl derivatives are useful as an antiprotozoan agent. As an antiprotozoan agent, PHM-3 acetate can be used advantageously as a reagent for testing the bacterial ecology of a soil, activated sludge or body fluid sample, for instance. Thus, when it is desired to separate useful bacteria from a soil sample or to test the activity of bacteria to the exclusion of that of protozoas in the operation and analysis of an activated sludge system for waste water treatment, the compound permits selective growth of bacterial flora without allowing the concomitant protozoas to growth. A specific procedure may comprise adding the sample to a liquid or solid medium, adding 0.1 ml of a 10% aqueous solution of methanol containing 100 to 400 $\mu g/ml$ of PHM acylate to each 1 ml of the medium and incubating the same medium.

C-15003 PHM and its acylate are capable of prolonging the life spans of tumor-bearing animals (e.g. mouse) and, therefore, are expected to be of value as antitumor agents.

Nocardia sp. No. N-1231 can be used as a high-potency antibiotics producer for the commercial production of C-15003, P-2, P-1 and P-0.

The following reference and working examples are given to further illustrate this invention. In these examples, all percents (%) are by weight/volume (w/v %) unless otherwise indicated.

REFERENCE EXAMPLE 1

Nocardia sp. No. C-14482 IFO-13887 strain (deposited in Fermentation Research Institute and in ATCC under the accession number of 31309) cultivated on a yeast extract-malt extract agar slant medium was used to inoculate 40 ml of a seed culture medium containing 2% of glucose, 3% of soluble starch, 1% of raw soybean flour, 1% of corn steep liquor, 0.5% of polypeptone, 0.3% of NaCl and 0.5% of $CaCO_3$ (pH 7.0) in a 200-milliliter conical flask, which was incubated on a rotary shaker at 28° C. for 48 hours. A 0.5 ml portion of the resultant seed culture was transferred to a 200-milliliter conical flask containing 40 ml of a main medium composed of 5% of dextrin, 3% of corn steep liquor, 0.1% of polypeptone, 1% of $CaCl_2$ and 0.5% of $CaCO_3$ (pH 7.0) and the inoculated main medium was incubated on a rotary shaker at 28° C. for 66 hours. The resultant fermentation broth was assayed by the agar dilution method using *Escherichia coli* K-12 (IFO-3301) and *Proteus mirabilis* (IFO-3849) as test organisms and C-14482 $B_1$ as the reference standard. The activity (potency) was found to be 10 μg/ml.

REFERENCE EXAMPLE 2

A 10 ml of the seed culture obtained in Reference Example 1 was transferred to a 2-liter Sakaguchi flask containing 500 ml of seed culture medium and the inoculated flask was incubated on a reciprocating shaker at 28° C. for 48 hours. The resultant culture (1 l) was used to inoculate a 200-liter stainless steel tank containing 100 l of seed culture medium, and cultivation was carried out at 28° C. with aeration at the rate of 100 l/min. and agitation at 200 r.p.m. for 48 hours to prepare a seed culture. This seed culture was transferred to a 2000-liter stainless steel tank containing 1500 liters of the main culture medium indicated in Reference Example 1 at an inoculation ratio of 10% and cultivation was carried out at 28° C., 1000 l/min. aeration, 150 r.p.m. (⅜ DT) and an internal pressure of 1 kg/$cm^2$ for 90 hours. The resultant fermentation broth was assayed by the method described in Reference Example 1. The activity (potency) was found to be 5 μg/ml.

REFERENCE EXAMPLE 3

The fermentation broth (1160 l) obtained in Reference Example 2 was adjusted to pH 5.0 with dilute sulfuric acid, and filtered with the addition of 35 kg of Hyflo-Supercel (Jhones-Manville Sales Corp., U.S.A.) The resultant filtrate (1180 l) was adjusted to pH 6.0 and passed through a column of 100 l of Diaion HP-10 (Mitsubishi Chemical Industries Ltd., Japan). After the column was rinsed with 300 l of water, elution was carried out with 400 l of 80% aqueous methanol.

The eluate was adjusted to pH 4.5 and concentrated under reduced pressure to distill off the methanol. The concentrate (60 l) was adjusted to pH 8.0 and extracted 3 times with 20 l portions of isobutyl alcohol. The isobutyl alcohol extracts were combined and washed twice with 35 l portions of 1/200 N-hydrochloric acid. The water layers were combined and concentrated at pH 4.5 under reduced pressure to distill off the isobutyl alcohol. The residual aqueous solution (40 l) was adjusted to pH 6.0 and adsorbed on a column of 25 liters of Diaion HP-10.

After the column was rinsed with 75 l of water, elution was carried out with 100 l of 80% aqueous methanol. The eluate was adjusted to pH 4.5 and concentrated under reduced pressure. The concentrate (2 l) was adjusted to pH 8.0 and extracted 5 times with 0.7 l of chloroform. The extracts were combined, concentrated under reduced pressure to 4 liters and washed twice with 0.5 l of 1/50 N-hydrochloric acid. The aqueous solution (1 l) was adjusted to pH 8.0 and re-extracted 5 times with 2 l portions of chloroform. The chloroform solution was dried over anhydrous sodium sulfate and concentrated under reduced pressue at low temperature to obtain 7.7 g of crude product (i).

The above crude product (7.7 g) was dissolved in 13 ml of MeOH, stirred with 80 ml of 0.1 N-HCl and 160 ml of water and filtered. The filtrate was diluted with water, adjusted to pH 6.0 and passed through a column of 500 ml Amberlite XAD-2 (Rohm & Haas Co., U.S.A.) The column was developed with 1.5 l of 5% aqueous methanol and 700 ml of a first active fraction was adjusted to pH 8.0 and extracted 5 times with 300 ml portions of $CHCl_3$. The extracts were combined, dehydrated over anhydrous sodium sulfate and concentrated under reduced pressure. The precipitated crystalline product was recovered by filtration and dried. The above procedure provides 849 mg of crude crystals of C-14482$B_1$. A 700 mg portion of this crude crystalline product was recrystallized from acetone-n-hexane to recover 360 mg of pure crystals of C-14482$B_1$. The mother liquor yielded a further 60 mg crop of C-14482$B_1$ crystals.

From the mother liquor giving said crude C-14482$B_1$ crystals, there was obtained 1.6 g of a mixture containing such active substances as C-14482$B_1$, $B_2$ and $B_3$.

On the other hand the concentrate (60 l) of the active fraction (400 l) from the first HP-10 column was extracted with isobutyl alcohol and the residual aqueous layer (50 l) was further concentrated to remove the isobutyl alcohol. The residue was passed through a column of 10 l of Amberlite IRC-50 (H-form) and after the column was rinsed with water, elution was carried out with 120 l of 0.2 N-hydrochloric acid.

The eluate was adjusted to pH 6.0 and adsorbed on a column of 25 l of Diaion HP-10. After the column was rinsed with 75 l of water, elution was carried out with 100 l of 80% aqueous methanol. The eluate was brought to pH 4.5 and concentrated under reduced pressure to 1.6 l. The concentrate was adjusted to pH 8.0 and extracted 5 times with 0.8 l portions of chloroform. The extracts were combined, dehydrated over anhydrous sodium sulfate and concentrated. The above procedure provided 2.5 g of a crude product (ii) containing C-14482$B_1$.

By purifying this crude product (ii) on a column of Amberlite XAD-2 in the same manner as above, there were obtained C-14482$B_1$ crystals and a mixture of C-14482$B_1$, $B_2$ and $B_3$.

C-14482$B_2$ was isolated in the following manner. The mother liquor after recovery of pure C-14482$B_1$ crystals from the above-mentioned crude product (i) was concentrated to dryness and the residue was extracted with a small amount of $CHCl_3$. The chloroform solution was concentrated to dryness again. The resultant mixture containing C-14482$B_1$ and $B_2$ was subjected to thin-layer chromatography on silica gel (Merck, Germany, HF$_{254}$) at low temperature [solvent system:ethyl acetate-methanol (3:2)] and the fraction corresponding to C-14482B$_2$ was scraped off and extracted with ethanol. The extract was concentrated and the concentrate was chromatographed on a column of Sephadex LH-20 (Pharmacia, Sweden) and elution was carried out with ethanol. The fractions corresponding to C-14482B$_2$ were pooled and concentrated, whereupon 10 mg of pure C-14482B$_2$ was obtained.

In addition, the mother liquor (1.6 g) after separation of crude C-14482B$_1$ crystals were also subjected repeatedly to silica gel (Merck, Germany, HF$_{254}$) TLC using chloroform-methanol (9:1) and ethyl acetate-methanol (3:2), followed by Sephadex LH-20 (Pharmacia, Sweden) column chromatography. The above procedure yielded 10 mg of C-14482B$_2$ and 4 mg of C-14482B$_3$.

The crystals of C-14482B$_1$ (as crystallized from acetone-hexane) and C-14482B$_2$ and B$_3$ as obtained in Reference Examples 1 through 4 have the following properties.

(a) C-14482B$_1$:
(I) Elemental analysis (%) (as crystallized from acetone-hexane and dried under reduced pressure at room temperature for at least 30 hours):
   C: 55.61±1.0,
   H: 6.31±0.5,
   N: 13.64±1.0.
(II) m.p. $\geq$300° C.
(III) Specific rotation: Not determinable (in ethanol)
(IV) Absorptions in ultraviolet and visible regions:
   $\lambda_{max}^{MeOH}$ (E$_{1\ cm}^{1\%}$) 213±3 nm (592±60),
   $\lambda_{max}^{MeOH}$ (E$_{1\ cm}^{1\%}$) 283±3 nm (227±25),
   $\lambda_{max}^{MeOH}$ (E$_{1\ cm}^{1\%}$) 496±3 nm (50.1±10).
(V) IR (KBr)
   Dominant peaks (cm$^{-1}$): 3580, 3420, 3175, 2950, 2900, 2840, 1685, 1650, 1610, 1445, 1395, 1345, 1330, 1250, 1230, 1175, 1110, 1075, 1025, 1000, 965, 940, 915, 855, 825, 780, 760.
(VI) Solubility:
   Insoluble: hexane, petroleum ether
   Sparingly soluble: ethyl acetate, chloroform, methylene chloride, diethyl ether, water,
   Soluble: ethanol,
   Readily soluble: methanol, dimethyl sulfoxide.
(VII) Color reactions:
   Negative: ninhydrin and Sakaguchi reactions,
   Positive: Dragendorff, Barton (gradually becomes blue), potassium permanganate (decolorized).
(VIII) Acidic, neutral or basic: Weakly basic
(IX) Color: Dark red to reddish brown
(X) Stability: When heated at 80° C. for 1 hour, slightly unstable at pH 3, 4 and 5; fairly unstable at pH 6 and unstable at pH 7 and 8.
(XI) TLC (silica gel; Spot Film f, Tokyo Kasei K.K., Japan)
   (1) Chloroform-methanol (9:1), Rf 0.37
   (2) Ethyl acetate-methanol (1:1), Rf 0.31

(b) C-14482B$_2$:
(I) Elemental analysis (%) (dried under reduced pressure at room temperature for at least 30 hours):
   C: 57.40±1.0
   H: 6.51±0.5
   N: 13.44±1.0
(II) m.p. $\geq$300° C.
(II) Absorptions in ultraviolet and visible regions:
   $\lambda_{max}^{MeOH}$ 2145±3 nm (E$_{1\ cm}^{1\%}$ 555±60),
   $\lambda_{max}^{MeOH}$ 283±3 nm (E$_{1\ cm}^{1\%}$ 207±25),
   $\lambda_{max}^{MeOH}$ 499±3 nm (E$_{1\ cm}^{1\%}$ 55.8±10).
(IV) IR (KBr)
   Dominant peaks (cm$^{-1}$): 3430, 2940, 2890, 1680, 1650, 1625, 1590, 1480, 1450, 1390, 1340, 1250, 1175, 1110, 1075, 1055, 1025, 995, 960, 940, 905, 855, 825.
(V) Solubility:
   Insoluble: hexane, petroleum ether,
   Sparingly soluble: ethyl acetate, diethyl ether, water,
   Soluble: ethanol, chloroform,
   Readily soluble: methanol, dimethyl sulfoxide.
(VI) Color reactions:
   Negative: ninhydrin and Sakaguchi reactions,
   Positive: Dragendorff, Barton (gradually becomes blue), potassium permanganate (decolorized).
(VII) Acidic, neutral or basic: Weakly basic
(VIII) Color: Dark red to reddish brown
(IX) TLC (silica gel, Spot Film f, Tokyo Kasei K.K., Japan)
   (1) Chloroform-methanol (9:1), Rf 0.43;
   (2) Ethyl acetate-methanol (1:1), Rf 0.23.

(c) C-14482 B$_3$:
(I) Elemental analysis (%) dried under reduced pressure at room temperature for at least 30 hours):
   C: 58.74±1.0,
   H: 6.64±0.5,
   N: 14.31±1.0.
(II) m.p. $\geq$300° C.
(III) Absorptions in ultraviolet and visible regions:
   $\lambda_{max}^{MeOH}$ 214±3 nm (E$_{1\ cm}^{1\%}$ 620±60),
   $\lambda_{max}^{MeOH}$ 283±3 nm (E$_{1\ cm}^{1\%}$ 251±25),
   $\lambda_{max}^{MeOH}$ 492±3 nm (E$_{1\ cm}^{1\%}$ 55.6±10).
(IV) IR (KBr)
   Dominant peaks (cm$^{-1}$): 3430, 2940, 2890, 1680, 1650 1630, 1595, 1450, 1390, 1340, 1320, 1250, 1175, 1105, 1075, 1020, 995, 935, 905, 825.
(V) Solubility:
   Insoluble: hexane, petroleum ether,
   Sparingly soluble: ethyl acetate, diethyl ether, water
   Soluble: ethanol, chloroform,
   Readily soluble: methanol, dimethyl sulfoxide.
(VI) Color reactions:
   Negative: ninhydrin and Sakaguchi reactions,
   Positive: Dragendorff, Barton (gradually becomes blue), potassium permanganate (decolorized).
(VII) Acidic, neutral or basic: Weakly basic.
(VIII) Color: Dark red to reddish brown.
(IX) TLC (silica gel, Spot Film f, Tokyo Kasei K.K., Japan)
   (1) Chloroform-methanol (9:1), Rf 0.20
   (2) Ethyl acetate-methanol (1:1), Rf 0.18

EXAMPLE 1

A slant culture of Nocardia sp. No. N-1231 (IFO 13963, ATCC 31565) on yeast extract-malt extract agar was used to inoculate a 200 ml conical flask containing 40 ml of a seed culture medium composed of 2% glucose, 3% soluble starch, 1% raw soybean flour, 1% corn steep liquor, 0.5% Polypepton (Daigo Nutritive Chemicals, Lt., Japan), 0.3% NaCl and 0.5% CaCO$_3$ (pH 7.0). The flask was incubated on a rotary shaker at 28° C. for 48 hours to obtain a seed culture. A 0.5 ml portion of this seed culture was transferred to a 200 ml conical flask containing 40 ml of a production medium composed of 5% dextrin, 3% corn steep liquor, 0.1% Polypepton and 0.5% CaCO$_3$ (pH 7.0) and cultivation was carried out on a rotary shaker at 28° C. for 90 hours. To this fermentation broth was added an equal volume of methanol and, after thorough stirring, the mixture was assayed for activity by the serial broth dilution method using *Tetrahymena pyriformis* W as the test organism and P-3 as the reference standard. The above mixture showed a total potency, inclusive of that of C-15003, of 100 μg/ml.

EXAMPLE 2

A 10 ml portion of the seed culture obtained in Example 1 was transferred to a 2-liter Sakaguchi flask containing 500 ml of a seed culture medium, and cultivation was carried out on a reciprocating shaker at 28° C. for 48 hours. The culture (1000 ml) was transferred to a 200-liter stainless steel tank containing 100 l of seed culture medium, and cultivation was carried out at 28° C., an aeration rate of 100 l/min., 200 r.p.m. (⅛ DT) and an internal pressure of 1 kg/cm² for 48 hours to obtain a seed culture. This seed culture was transferred to a 200-liter stainless steel tank containing 100 l of the same production medium as that shown in Example 1 (inoculum size: 5%), and cultivation was carried out at 28° C., 100 l/min. aeration, 170 r.p.m. (⅛ DT) and an internal pressure of 1 kg/cm² for 90 hours. The resulting culture broth was assayed for activity by the same assay procedure as that used in Example 1. The total titer, inclusive of that of C-15003, was 70 μg/ml.

EXAMPLE 3

To 100 l of the culture broth obtained in Example 2 were added 4 kg of Hyflo-Supercel (Jhones-Manville Sales Corp., U.S.A.) and 200 l of ethyl acetate, followed by thorough stirring. The mixture was filtered in a pressure filter, and after standing, the water layer was discarded, which left 180 l of an ethyl acetate layer. The ethyl acetate layer was washed with 40 l of 1/5 M aqueous sodium carbonate, washed with water and concentrated under reduced pressure to 200 ml, followed by addition of petroleum ether. The resultant precipitate was recovered to obtain 18 g of crude product (i).

EXAMPLE 4

The procedures of Example 1, 2 and 3 were repeated, and 10 batches of crude product (i) (a total of 172 g) were stirred with 300 ml of chloroform. The insoluble fraction was filtered and the filtrate was stirred with 50 g of silica gel (Merck, Germany, 0.063–0.2 mm). The chloroform was distilled off under reduced pressure and the residue was applied to the top of a silica gel column (2 l). Then, elution was carried out with 2 l of chloroform, 2 l of chloroform-methanol (50:1), 4 l of the same (25:1) and 4 l of the same (9:1) in that order. The eluate was collected in 500 ml fractions and a 1 ml portion of each fraction was concentrated to dryness. To each concentrate was added 0.1 ml of chloroform and the mixture was spotted on a silica gel glass plate (Merck, Germany, Kieselgel 60F254, 0.25 mm, 20×20 cm) at 2.5 cm from the bottom edge. The chromatogram was developed over about 17 cm with chloroform-methanol (9:1). After development, the plate was irradiated with ultraviolet light (2537 Å) and the fractions No. 20 to No. 23 which absorbed in the neighborhood of Rf 0.27 to 0.32 were collected and concentrated under reduced pressure to about 20 ml. To the concentrate was added 150 ml of petroleum ether, whereupon 3.1 g of crude product (ii) was obtained.

EXAMPLE 5

To 3 g of the crude product obtained in Example 4 was added 30 ml of chloroform and, after stirring, the insolubles were removed by filtration. The filtrate was stirred with 8 g of silica gel (Merck, Germany, samd as above) and the chloroform was distilled off under reduced pressure. The residue was applied to the top of a silica gel column (200 ml) and elution was carried out with 2 l of $H_2O$-saturated ethyl acetate and 1 l of $H_2O$-saturated ethyl acetate-water (10:1), the eluate being collected in 20 ml fractions. Each fraction was spotted on a silica gel glass plate (Merck, Germany, same as above) and after development with $H_2O$-saturated ethyl acetate, detection was carried out with ultraviolet light. The fractions No. 112 to No. 146 which absorbed in the neighborhood of Rf 0.09 to 0.19 were collected and concentrated to dryness. The residue was dissolved in small amounts of methanol and ethyl acetate, followed by addition of petroleum ether, whereby 62 mg of powder containing PHM-4, PHM-3, PHM-2 and PHM-1 were obtained. A 60 mg portion of the above powder was dissolved in 1 ml of chloroform and applied onto 20 silica gel glass plates (Merck, Germany, same as above) linearly at 2.5 cm from the bottom edge. Each chromatogram was developed with $H_2O$-saturated ethyl acetate. After development over about 17 cm, the absorbing zones at Rf 0.19 (PHM-4), Rf 0.16 (PHM-3), Rf 0.13 (PHM-2) and Rf 0.09 (PHM-1) were scraped off and with the addition of a small amount of water, extracted 3 times with chloroform. The chloroform layer was washed with water, dried over anhydrous sodium sulfate and concentrated to dryness under reduced pressure. To the residue were added small amounts of methanol and ethyl acetate and the mixture was allowed to stand. The above procedure yielded crystals: 11 mg of PHM-4 from the fraction at Rf 0.19, 26 mg of PHM-3 from the fraction at Rf 0.16, 3 mg of PHM-2 from the fraction at Rf 0.13 and 1 mg of PHM-1 from the fraction at Rf 0.09.

EXAMPLE 6

Out of the fractions obtained by silica gel column chromatography in Example 4, the silica gel TLC fractions absorbing in the neighborhood of Rf 0.50 to 0.58 (Nos. 13 to 15; Fraction-A), those absorbing in the neighborhood of Rf 0.48–0.50 (Nos. 16–17, Fraction-B) and those absorbing in the neighborhood of Rf 0.33 to 0.38 (No. 18, Fraction-C) were respectively pooled and concentrated to dryness under reduced pressure. To the residue of Fraction-A was added 150 ml of ethyl acetate, while 20 ml of ethyl acetate was added to the residue of Fraction-B. Each mixture was warmed and, after removal of insolubles by filtration, the filtrate was allowed to stand at room temperature. In the above manner, Fraction-A yielded 61 g of crude crystals containing P-4, P-3', P-3 and P-2, and Fraction-B yielded 3.3 g of crude crystals containing P-3, P-2 and P-1. To the residue of Fraction-C was added 50 ml of ethyl acetate and after filtration of insolubles, the filtrate was concentrated under reduced pressure to 5 ml, followed by addition of 50 ml of petroleum ether. This procedure yielded 1.8 g of a crude powder containing P-1 and P-0.

EXAMPLE 7

In 300 ml of chloroform were dissolved 61 g of crude crystals from Fraction-A of Example 6 and the solution was stirred well with 100 g of silica gel (same as above).

The chloroform was then distilled off under reduced pressure and the residue was applied to the top of a silica gel column (2 l). Then, elution was carried out with 2 l of H$_2$O-saturated n-hexane-ethyl acetate (1:4), 3 l of H$_2$O-saturated n-hexane-ethyl acetate (1:5), 2 l of H$_2$O-saturated n-hexane-ethyl acetate (1:7) and 3 l of H$_2$O-saturated ethyl acetate. The eluate was collected in 100 ml fractions. Each fraction was spotted onto a silica gel glass plate (same as above) and after development with H$_2$O-saturated ethyl acetate, the fraction giving a single spot was taken and concentrated to dryness under reduced pressure. Each residue was dissolved in 4 to 5 times its amount of ethyl acetate (V/W) under warming to obtain the following crystals.

Rf 0.49, P-4 (15.6 g),
Rf 0.42, P-3 (12.8 g),
Rf 0.38, P-2 (6.92 g),
Rf 0.34, P-1 (0.56 g).

In addition, 18.7 g of mixed crystals of P-3 and P-2 were obtained.

The fractions absorbing in the neighborhood of Rf 0.45 were collected, concentrated to dryness under reduced pressure and crystallized from ethyl acetate to obtain crystals (124 mg) containing P-4 and P-3'. In 2 ml of chloroform were dissolved 63 mg of mixed crystals of P-4 and P-3' and the solution was applied linearly to each of 30 silica gel glass plates (same as above) at 2.5 cm from the bottom edge. Each chromatograph was developed with H$_2$O-saturated ethyl acetate. The fractions absorbing at Rf 0.45 were scraped off and extracted twice with ethyl acetate containing a small amount of water. The ethyl acetate extract was washed with water, dried over anhydrous sodium sulfate, concentrated under reduced pressure and allowed to stand, whereupon P-3' crystals were obtained (52 mg).

EXAMPLE 8

The crude crystals (3.3 g) from Fraction-B of Example 6 were treated in the same manner as Example 7 to obtain the following crystals.

Rf 0.42, P-3 (840 mg),
Rf 0.38, P-2 (276 mg),
Rf 0.34, P-1 (126 mg).

The physicochemical properties of these P-3, P-2 and P-1 crystals were respectively in agreement with those of the P-3, P-2 and P-1 crystals obtained in Example 7.

EXAMPLE 9

The crude powder (1.8 g) from Fraction-C of Example 6 was treated in the same manner as Example 7 to obtain the following crystals.

Rf 0.34, P-1 (36 mg)
Rf 0.23, P-0 (98 mg)

The properties of this P-1 were in agreement with those of the P-1 crystals obtained in Example 7.

The physicochemical properties of the P-0, P-1, P-2, P-3, P-3' and P-4 obtained in accordance with Examples 7 and 9 are presented below in Tables 4 and 5. These properties are in good agreement with the corresponding descriptions given in Tetrahedron 35, 1079 and Nature, Vol. 270, p. 721 (1977).

TABLE 4

| | P-0 $C_{28}H_{37}ClN_2O_8$ | | P-1 $C_{30}H_{39}ClN_2O_9$ | | P-2 $C_{31}H_{41}ClN_2O_9$ | |
|---|---|---|---|---|---|---|
| m.p. (°C.) | 198–200 | | 235–236 | | 188–190 | |
| Specific rotation $[\alpha]_D^{24}$ | −195° (c = 0.46, CHCl$_3$) | | −124° (c = 0.48, CHCl$_3$) | | −130° (c = 0.45, CHCl$_3$) | |
| UV absorption spectrum, nm ($\epsilon$) | 233 | (32500) | 233 | (30300) | 233 | (30100) |
| | 244sh | (30600) | 240sh | (28000) | 240sh | (28300) |
| | 252 | (31400) | 252 | (27800) | 252 | (27550) |
| | 281 | (5730) | 280 | (5420) | 280 | (5730) |
| | 288 | (5680) | 288 | (5420) | 288 | (5710) |
| Mass spectrum m/e | 503, 485, 468, 451 | | 545, 485, 470, 450 | | 559, 485, 470, 450 | |

TABLE 5

| | P-3 $C_{32}H_{43}ClN_2O_9$ | | P-3' $C_{32}H_{43}ClN_2O_9$ | | P-4 $C_{33}H_{45}ClN_2O_9$ | |
|---|---|---|---|---|---|---|
| m.p. (°C.) | 189–191 | | 181–184 | | 177–179 | |
| Specific rotation $[\alpha]_D^{24}$ | −134° (c = 0.54, CHCl$_3$) | | −131° (c = 0.25, CHCl$_3$) | | −140° (C = 0.48, CHCl$_3$) | |
| UV absorption spectrum, nm ($\epsilon$) | 233 | (30150) | 233 | (30150) | 233 | (29900) |
| | 240sh | (28500) | 240sh | (28300) | 240sh | (28260) |
| | 252 | (27600) | 252 | (27500) | 252 | (27500) |
| | 280 | (5740) | 280 | (5730) | 280 | (5700) |
| | 288 | (5700) | 288 | (5700) | 288 | (5670) |
| Mass spectrum m/e | 573, 485, 470 450 | | 573, 485, 470, 450 | | 587, 485, 470, 450 | |

EXAMPLE 10

In 0.2 ml of pyridine was dissolved the PHM-3 (13 mg) obtained in Example 5 and after addition of 0.1 ml of acetic anhydride, the solution was allowed to stand at room temperature overnight. The reaction mixture was concentrated to dryness under reduced pressure and the residue was subjected to preparative thin-layer chromatography with 3 silica gel glass plates (same as above). After development with H$_2$O-saturated ethyl acetate, the fraction absorbing at Rf 0.37 was scraped off and extracted with ethyl acetate containing a small amount of water. The extract was washed with water, dried over anhydrous sodium sulfate and concentrated under reduced pressure. The above procedure provided crystals (9 mg) of the compound that the CH$_2$OH in 14-position of PHM-3 had been acetylated, m.p. 240°–242° C.

Mass spectrum (m/e): 692, 631, 571, 556, 536, 483, 468, 448.

NMR spectrum (90 MHz, deuteriochloroform): δ2.07 (3H,s).

EXAMPLE 11

In 0.5 ml of pyridine was dissolved 30 mg of PHM-3 and, after addition of 4 drops of isovaleric acid and 130 mg of dicyclohexylcarbodiimide, the solution was allowed to stand at room temperature overnight. To the reaction solution was added 2 ml of methanol, the precipitates were filtered off and the filtrate was concentrated. To the concentrate was added 30 ml of ethyl acetate and the insolubles were filtered off. The ethyl acetate solution was washed with dilute hydrochloric acid, aqueous sodium bicarbonate solution and water in the order mentioned, dried and concentrated to dryness under reduced pressure.

The residue was crystallized from the mixed solvent of methylene chloride and petroleum ether, thus yeilding 23 mg of PHM-3 isovalerate, m.p. 144°–146° C.

Mass spectrum (m/e): 734, 673, 571, 556, 536, 483, 468, 448,

TLC (Merck, Germany, silica gel glass plate F254, 0.25 mm, developing solvent: water-saturated ethyl acetate) Rf: 0.53.

EXAMPLE 12

In 0.5 ml of pyridine was dissolved 50 mg of PHM-3 and, after addition of 6 drops of n-butyric anhydride, the solution was allowed to stand at room temperature overnight. After addition of 2 ml of methanol to the reaction solution, the solution was concentrated and to the residue was added 50 ml of ethyl acetate. The ethyl acetate solution was washed with dilute hydrochloric acid, aqueous sodium bicarbonate solution and water in the order mentioned, dried and concentrated to dryness under reduced pressure.

The residue was crystallized from ethyl acetate to give 46 mg of PHM-3 n-butyrate, m.p. 195°–197° C.

Mass spectrum (m/e): 720, 659, 571, 556, 536,

TLC (the same conditions as those of Example 11), Rf: 0.50.

EXAMPLE 13

In 0.5 ml of pyridine was dissolved 50 mg of PHM-3 and after addition of 50 mg of benzoic anhydride, the solution was allowed to stand at room temperature overnight. The reaction solution was treated by the procedures similar to those of Example 12. The residue thus obtained was dissolved in a small amount of ethyl acetate and to the solution was added petroleum ether to give white powder. The powder was washed with ether, thus yeilding 48 mg of PHM-3 benzoate.

Mass spectrum (m/e): 754, 693, 571, 556, 536.

TLC (the same conditions as those of Example 11), Rf: 0.50.

What we claim is:

1. A biologically pure culture of *Nocardia* sp. No. N-1231, ATCC 31565, which is capable of producing antibiotic C-15003 PHM of the structural formual.

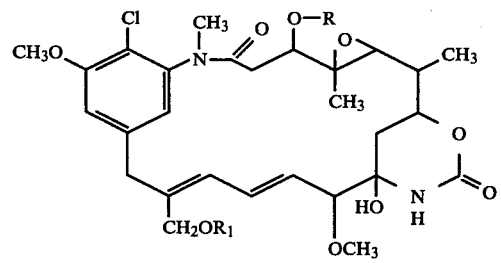

wherein R is —COCH$_3$, —COCH$_2$CH$_2$,

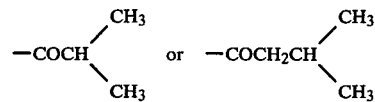

and R$_1$ is hydrogen.

* * * * *